United States Patent
Pradhan (12) 
(10) Patent No.: US 11,123,215 B2
(45) Date of Patent: Sep. 21, 2021

(54) PRESSURE RELIEF APPARATUS FOR WOUND

(71) Applicant: Renuka Pradhan, Bridgewater, NJ (US)

(72) Inventor: Renuka Pradhan, Bridgewater, NJ (US)

(*) Notice: Subject to any disclaimer, the term of this patent is extended or adjusted under 35 U.S.C. 154(b) by 407 days.

(21) Appl. No.: 15/678,177

(22) Filed: Aug. 16, 2017

(65) Prior Publication Data
US 2018/0049908 A1 Feb. 22, 2018

Related U.S. Application Data

(60) Provisional application No. 62/375,512, filed on Aug. 16, 2016.

(51) Int. Cl.
*A61F 5/32* (2006.01)
*A61F 13/00* (2006.01)
(Continued)

(52) U.S. Cl.
CPC .......... *A61F 5/32* (2013.01); *A61F 13/00017* (2013.01); *A61F 13/00042* (2013.01);
(Continued)

(58) Field of Classification Search
CPC ................ A61F 13/00; A61F 13/00017; A61F 13/00042; A61F 13/00068; A61F 5/32; A61F 5/30; A61F 13/124; A61F 13/063; A61F 13/064; A61F 13/065; A61F 13/067; A61F 13/101; A61F 13/102; A61F 2013/00497; A61F 2013/00557; A61F 2013/15024; A61F 5/3707; A61F 13/10; A61F 13/069; A61F 13/06;
(Continued)

(56) References Cited

U.S. PATENT DOCUMENTS 2,905,174 A * 9/1959 Smith ................. A61F 13/0206
602/42
2,918,062 A * 12/1959 Scholl ................. A61F 13/0246
128/894
(Continued)

OTHER PUBLICATIONS

Bluestein et al., "Pressure Ulcers: Prevention, Evaluation, and Management", American Family Physician, vol. 78, No. 10, Nov. 15, 2008, retrieved from http://www.aafp.org/afp/2008/1115/p1186.pdf, pp. 1186-1194.
(Continued)

*Primary Examiner* — Victoria J Hicks
*Assistant Examiner* — Kevin S Albers
(74) *Attorney, Agent, or Firm* — William J. Connelly, III; John Maldjian; Stevens & Lee PC (57) ABSTRACT

A pressure relief apparatus is provided for a wound on a patient body. The pressure relief apparatus includes a pliable body including a first surface and a second surface opposite to the first surface. The first surface contacts with the patient body. Further, the pliable body defines an aperture that is sized to surround the wound. The pliable body is made of a washable foam material. The pressure relief apparatus further includes at least one fastening member attached to the pliable body, wherein the at least one fastening member detachably secures the pliable body to a portion of the patient body.

17 Claims, 9 Drawing Sheets

(51) Int. Cl.
   *A61F 13/02* (2006.01)
   *A61L 15/42* (2006.01)
   *A61F 13/06* (2006.01)
   *A61L 15/26* (2006.01)
   *A61F 13/10* (2006.01)

(52) U.S. Cl.
   CPC .... *A61F 13/00068* (2013.01); *A61F 13/0206* (2013.01); *A61F 13/06* (2013.01); *A61F 13/065* (2013.01); *A61F 13/069* (2013.01); *A61F 13/10* (2013.01); *A61L 15/26* (2013.01); *A61L 15/42* (2013.01); *A61L 15/425* (2013.01); *A61F 13/102* (2013.01); *A61F 2013/0028* (2013.01)

(58) Field of Classification Search
   CPC ................. A61F 13/0206; A61F 5/006; A61F 2013/00468; A61F 2013/00174; A61F 2013/00387; A61F 13/061; A61F 13/062; A61F 13/068; A61F 13/108; A61F 2005/0181; A61F 2005/0183; A61F 2005/0186; A61F 2013/0028; A61F 2013/00463; A61F 2013/00472; A61F 5/019; A61F 7/08; A61F 7/02; A61F 2007/0225; A61F 2007/0228–0231; A61F 5/34; A61F 13/141; A61F 13/107; A47G 2009/1018; A61L 15/425; A61L 15/26; A61L 15/42; A61B 17/1325; A41D 13/05; A41D 13/055–0593
   USPC ............... 602/60, 41; 606/201; 128/889–894
   See application file for complete search history.

(56) References Cited

U.S. PATENT DOCUMENTS

| | | | |
|---|---|---|---|
| 3,209,750 A * | 10/1965 | Levitt .................... | A61F 5/019 128/894 |
| 4,006,741 A * | 2/1977 | Arluck .................. | A61F 5/0118 602/7 |
| 4,278,079 A * | 7/1981 | Simhoni ............... | A61F 13/069 128/892 |
| 4,409,975 A * | 10/1983 | Simhoni ............... | A61F 13/069 128/892 |
| 6,920,881 B2 | 7/2005 | Narula et al. | |
| 7,182,085 B1 * | 2/2007 | Larsen ................. | A61F 13/0203 128/846 |
| 7,252,871 B2 | 8/2007 | Crkvenac et al. | |
| 7,622,629 B2 | 11/2009 | Aali | |
| 7,725,951 B2 * | 6/2010 | Rampersad ........ | A41D 13/0556 2/24 |
| 8,252,970 B2 | 8/2012 | Buckman et al. | |
| 8,439,894 B1 | 5/2013 | Miller | |
| 8,444,611 B2 | 5/2013 | Wilkes et al. | |
| 8,491,513 B2 | 7/2013 | Flam et al. | |
| 8,722,960 B2 | 5/2014 | Aali et al. | |
| 2002/0007136 A1 * | 1/2002 | Narula .................. | A61F 13/069 602/46 |
| 2002/0138030 A1 * | 9/2002 | Cavanagh ............. | A61F 13/063 602/41 |
| 2004/0260225 A1 | 12/2004 | Bishop et al. | |
| 2006/0189909 A1 * | 8/2006 | Hurley .................. | A61F 13/063 602/41 |
| 2006/0243435 A1 | 11/2006 | Faul | |
| 2007/0163048 A1 | 7/2007 | Kimball | |
| 2007/0191754 A1 * | 8/2007 | Aali ...................... | A61F 15/008 602/58 |
| 2009/0069737 A1 | 3/2009 | Stapley et al. | |
| 2009/0270820 A1 | 10/2009 | Johnson et al. | |
| 2010/0204631 A1 | 8/2010 | Rooney | |
| 2011/0015708 A1 * | 1/2011 | Lee ........................ | A61F 5/0193 607/112 |
| 2012/0253302 A1 | 10/2012 | Corley | |
| 2013/0018294 A1 * | 1/2013 | Jones .................... | A61F 5/0106 602/27 |
| 2013/0218105 A1 * | 8/2013 | Blumenfeld ........ | A63B 71/1225 604/293 |
| 2014/0121649 A1 * | 5/2014 | Calco .................... | A61M 27/00 604/543 |
| 2014/0295135 A1 * | 10/2014 | Thompson, Jr. ........ | B32B 3/266 428/138 |
| 2014/0343520 A1 | 11/2014 | Bennett et al. | |
| 2015/0057624 A1 * | 2/2015 | Simmons ............ | A61F 13/0223 604/319 |
| 2015/0202354 A1 | 7/2015 | Wall | |
| 2019/0151157 A1 * | 5/2019 | Herder .............. | A61F 13/00063 |

OTHER PUBLICATIONS

Kirman et al., "Pressure Ulcers and Wound Care Treatment & Management", General Surgery, Jun. 20, 2016, retrieved from http://emedicine.medscape.com/article/190115-treatment#d7, 10 Pages.
A.D.A.M., "Corns and Calluses In-Depth Report", New York Times Health, 2008, retrieved on Jun. 28, 2016 from http://www.nytimes.com/health/guides/disease/corns-and-calluses/print.html, 12 Pages.

* cited by examiner

PRESSURE RELIEF APPARATUS FOR WOUND

CROSS-REFERENCE TO RELATED APPLICATIONS

This application claims the benefit of U.S. Provisional Application Ser. No. 62/375,512, filed on Aug. 16, 2016, the entire content of which is hereby incorporated by reference in its entirety.

FIELD OF THE INVENTION

Embodiments in accordance with the present disclosure relate to a pressure relief apparatus for use by people recovering from a wound, sore, or the like. The pressure relief apparatus promotes faster recovery and results in reduced risk of complications, such as infections.

BACKGROUND

When a person has a wound (e.g., a cut, a sore, a burn, etc.), physical pressure on or immediately adjacent to the wound affects the speed of recovery by the patient. Application of pressure may tend to interfere with recovery, such as by restricting blood flow. A longer recovery time also increases a risk that the wound may become infected. Speed of recovery is improved by removing pressure on or immediately adjacent to the wound.

Some traditional ways for promoting the healing of wounds include cleansing the wound area, debriding, and then covering the wound area with a dressing. A wound will often ooze an exudate before it is completely healed. The exudate has to be cleaned periodically from the wound and the surrounding area, and contaminated dressing has to be replaced. The wound area should be protected from the adverse effects of pressure, friction, and shear. For example, the wound area can be supported on a low-air-loss mattress or on an air-fluidized bed. However, such support may still impart an undesirable amount of pressure on wounds. Further, such supports may also become contaminated with exudate.

Therefore, a need exists for a pressure relief apparatus to help promote wound healing.

SUMMARY

Embodiments of the present disclosure generally relate to an improved pressure relief apparatus for wound care management, and, in particular to an apparatus that removes pressure from a wound, allowing the wound to heal faster. Embodiments may be reusable, e.g., by making soiled portions either washable or disposable. Embodiments also may be fire resistant.

Embodiments in accordance with the present disclosure provide an apparatus for the prevention and relief from pressure being applied directly upon a wound. Embodiments are applicable to substantially any size of wound, and substantially any stage of a wound or pressure ulcer on any area of the body, such as shoulder blades, back, elbows, sacrum, buttocks, trochanter, heels, plantar, toes, and so forth. Embodiments may also be used for wounds related to arterial insufficiency, or related to surgical wounds on substantially any part of the body where pressure is applied. Embodiments may also be used for prevention and relief of pressure on amputation site wounds, and diabetic wounds.

Embodiments in accordance with the present invention further provide a pressure relief apparatus which includes a body defining an aperture that is sized to surround the wound. The apparatus relieves pressure from the wound and aids in the healing process.

Embodiments in accordance with the present invention further provide a pressure relief apparatus which is made of a foam material that is washable and reusable. The foam material may also be fire retardant, and soft on delicate and fragile skin. In other embodiments of the present invention, the pressure relief apparatus may be sterilized before use on an individual.

Embodiments in accordance with the present invention further provide a pressure relief apparatus that can be easily secured to patient body using adhesive tape, secured to inner clothing or by adjustable strap(s) having snap fasteners, a hook-and-loop fastener such as Velcro®, etc.

Embodiments in accordance with the present invention further provide a pressure relief apparatus which includes a pliable body for added fit and flexibility for use with a wound and to assist in the healing process. In alternate embodiments of the present invention, the pliable body may be made of a foam material or similar materials, including but not limited to, polyethylene and polyurethane foams. The pliable body may be washable and reusable.

Embodiments in accordance with the present invention provide a pressure relief apparatus including an absorbent layer that absorbs exudate from the wound to prevent infection. Further, the absorbent layer is removable, disposable, and replaceable.

Embodiments in accordance with the present invention are directed to a pressure relief apparatus for a wound on a patient body. The pressure relief apparatus includes a body including a first surface and a second surface opposite to the first surface. The first surface contacts with the patient body. Further, the body defines an aperture that is sized to surround the wound. The body is made of a washable foam material. The pressure relief apparatus further includes at least one fastening member attached to the body, wherein the at least one fastening member detachably secures the body to a portion of the patient body. In other embodiments of the present invention, the fastener may disposed on any suitable location on the body.

Embodiments in accordance with the present invention are further directed to a pressure relief apparatus for a wound on a patient body. The pressure relief apparatus includes a body including a first part that contacts with the patient body. The first part defines an aperture that is sized to surround the wound. The body further includes a second part that is coupled with the first part. The body also includes at least one fastening member retained between the first part and the second part of the body, wherein the at least one fastening member detachably secures the body to a portion of the patient body. Each of the first part and the second part of the body is made of a washable foam material.

Other embodiments of the present invention are further directed to a pressure relief apparatus for a wound on a patient body. The pressure relief apparatus comprises a body having a bottom portion that contacts the patient body, an aperture sized to surround the wound and at least one fastener to secure the body of the pressure relief apparatus to the patient body. In yet another embodiment of the present invention, the body of the pressure relief apparatus may contain an opening to accept and detachably secure a fastener to secure the body of the pressure relief apparatus to the patient body. The fastener may be an adjustable strap an adjustable strap provided with a length adjustment mechanism such as, but not limited to, a buckle, Velcro, and so forth. In some embodiments, the fastener may be made of gauze, linen, cotton, polyester cotton blend or any other soft fabric. In some other embodiments, the fastener may be of an elastic material in order to accommodate different shapes and sizes of body parts of the patient. In yet another embodiment, the material of each of the fastener depends upon the mobility and the condition of the patient. Further, the size and type of the pair of the fastener may depend upon space, body shape and size limitations. In an alternative embodiment, the fastener may also be an adhesive strip. The fastener, as well as the opening may disposed on any suitable location on the body.

Yet other embodiments of the present invention are directed to a pressure relief apparatus for a wound on a patient body. The pressure relief apparatus includes a body including a first surface and a second surface opposite to the first surface. The first surface contacts with the patient body. The body further defines an aperture that is sized to surround the wound, The body is made of a washable foam material. The pressure relief apparatus also includes an absorbent layer disposed on at least a portion of the first surface. The absorbent layer is configured to absorb exudate from the wound. The pressure relief apparatus further includes at least one fastening member attached to the body. The at least one fastening member detachably secures the body to a portion of the patient body.

These and other advantages will be apparent from the present application of the embodiments described herein.

The preceding is a simplified summary to provide an understanding of some embodiments of the present disclosure. This summary is neither an extensive nor exhaustive overview of the present disclosure and its various embodiments. The summary presents selected concepts of the embodiments of the present disclosure in a simplified form as art introduction to the more detailed description presented below. As will be appreciated, other embodiments of the present disclosure are possible utilizing, alone or in combination, one or more of the features set forth above or described in detail below.

BRIEF DESCRIPTION OF THE DRAWINGS

The accompanying drawings, which are incorporated in and constitute a part of this specification, illustrate several embodiments of the disclosure and, together with the description, explain the principles of the disclosure.

FIC. 1C illustrates a back view of the pressure relief apparatus of the FIG. 1A.

While embodiments of the present disclosure are described herein by way of example using several illustrative drawings, those skilled in the art will recognize the present disclosure is not limited to the embodiments or drawings described. It should be understood the drawings and the detailed description thereto are not intended to limit the present disclosure to the form disclosed, but to the contrary, the present disclosure is to cover all modification, equivalents and alternatives falling within the spirit and scope of embodiments of the present disclosure as defined by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The present disclosure is related to a pressure relief apparatus for a wound on a patient body. The pressure relief apparatus includes a body including a first surface and a second surface opposite to the first surface. The first surface contacts with the patient body. Further, the body defines an aperture that is sized to surround the wound. The body is made of a washable foam material. The pressure relief apparatus further includes at least one fastening member attacked to the body, wherein the at least one fastening member detachably secures the body to a portion of the patient body.

Figure 1A:
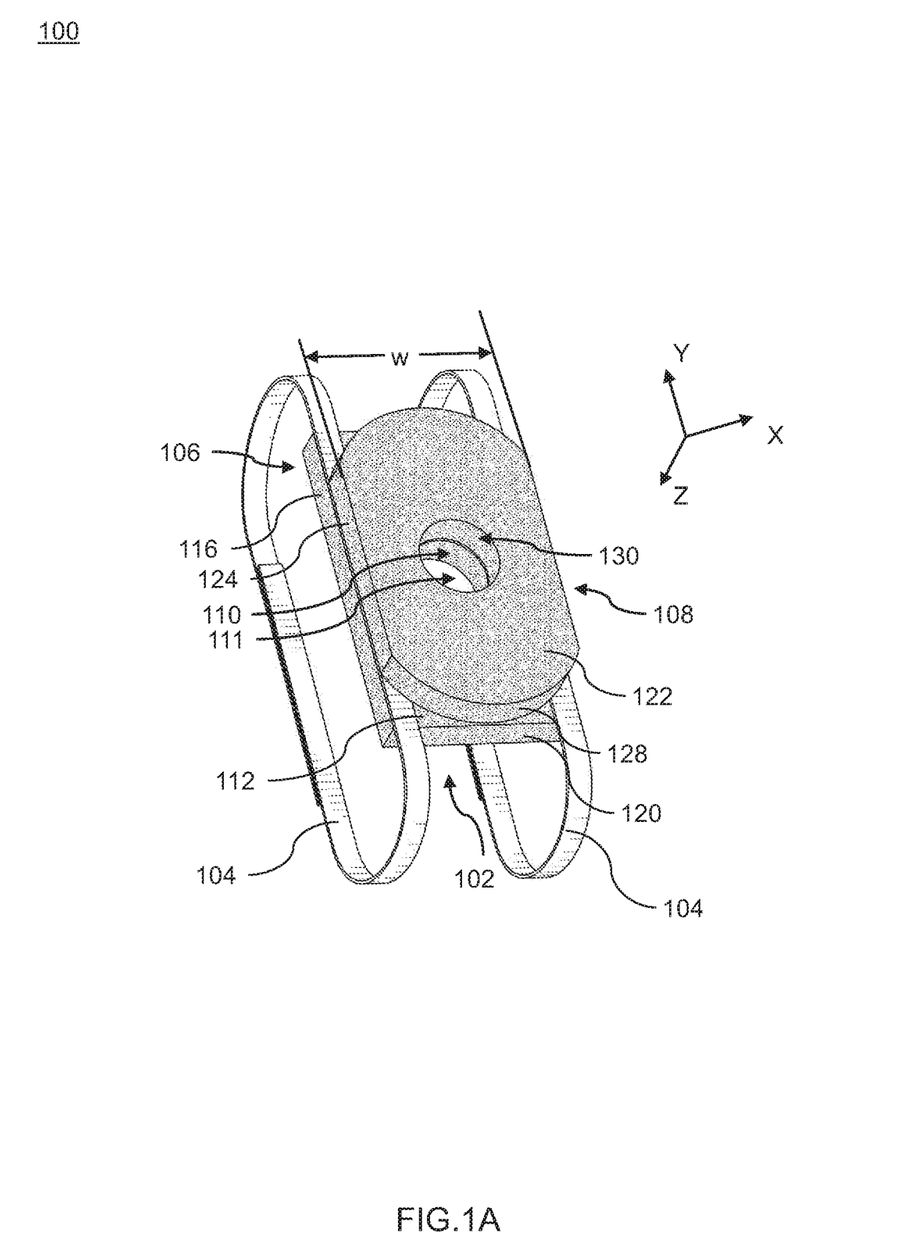
FIG. 1A illustrates a perspective view of a pressure relief apparatus, in accordance with an embodiment of the present disclosure.
Figure 1B:
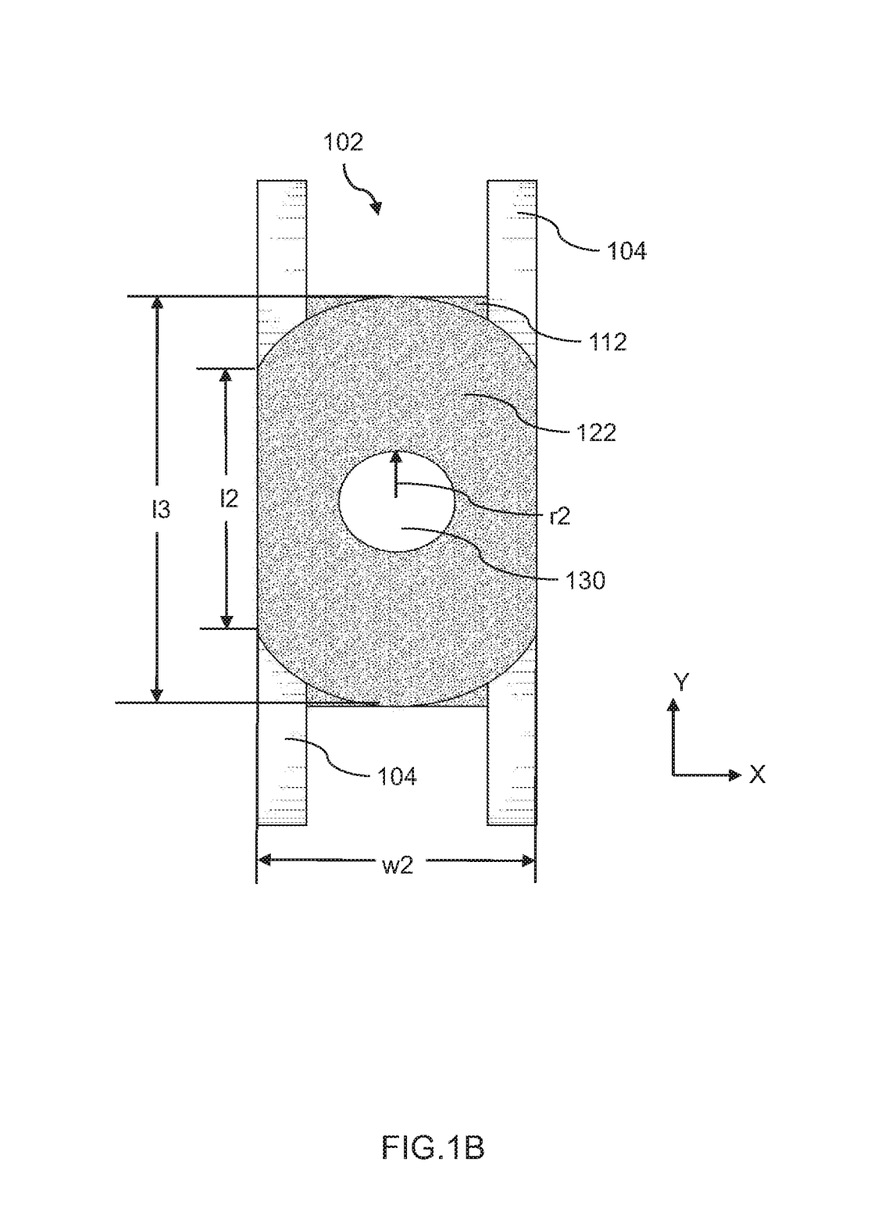
FIG. 1B illustrates a front view of the pressure relief apparatus of the FIG. 1A.
Figure 1C:
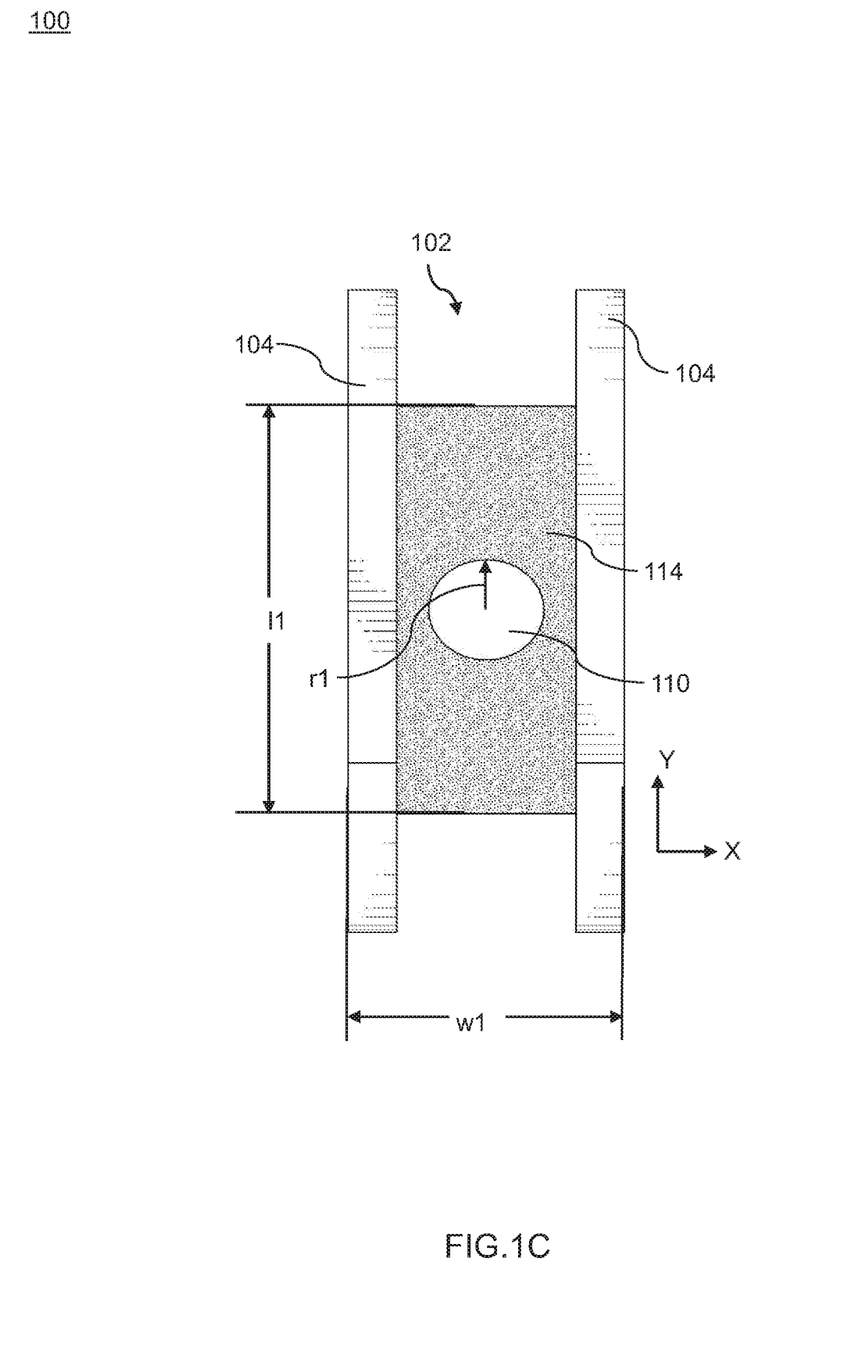
Figure 1D:
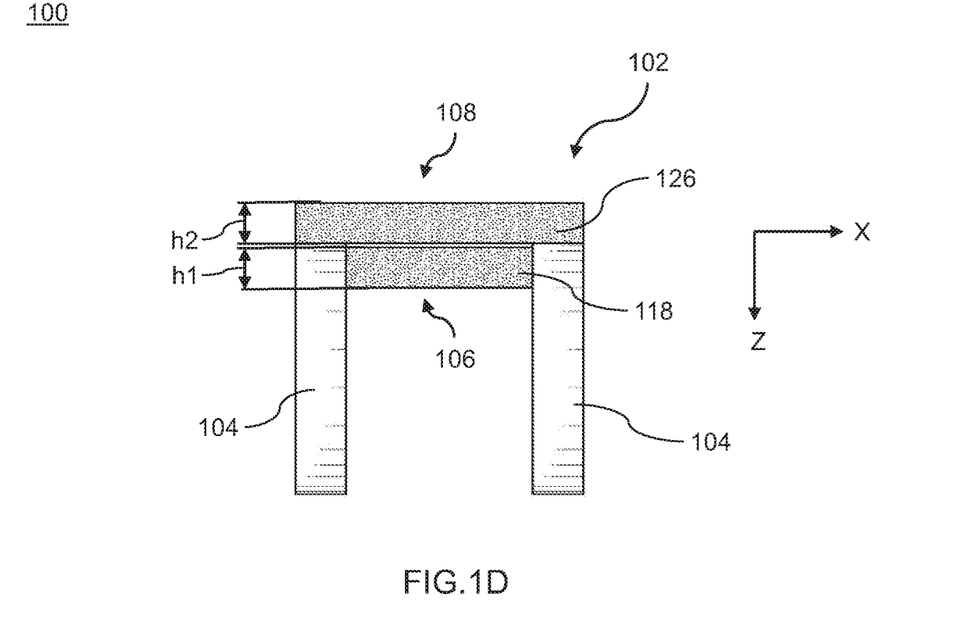
FIG. 1D illustrates a top view of the pressure relief apparatus of the FIG. 1A.
Figure 1E:
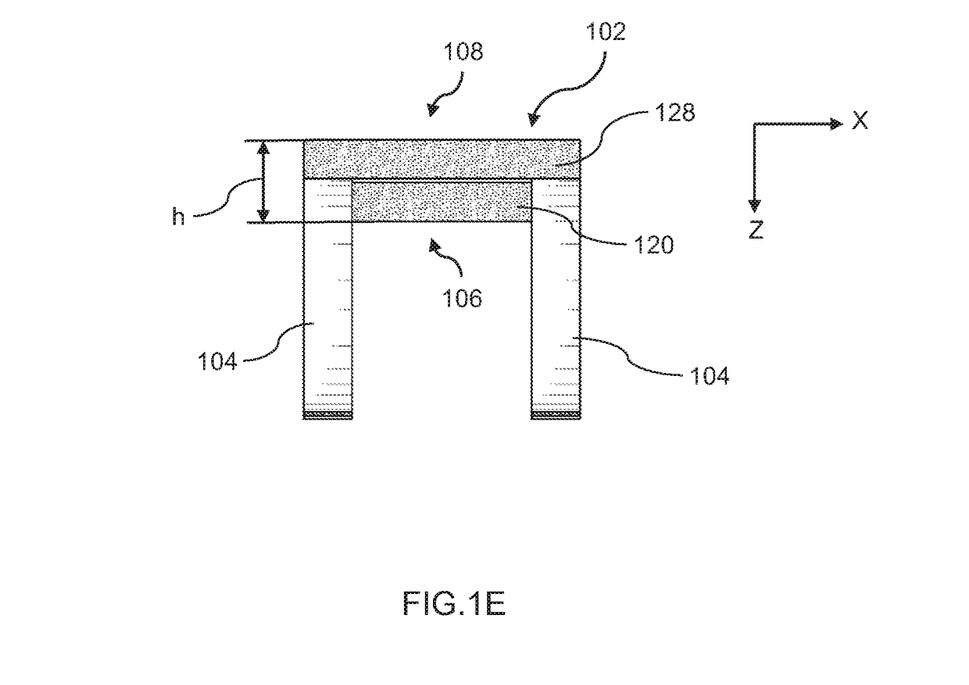
FIG. 1E illustrates a bottom view of the pressure relief apparatus of the FIG. 1A.
Figure 1F:
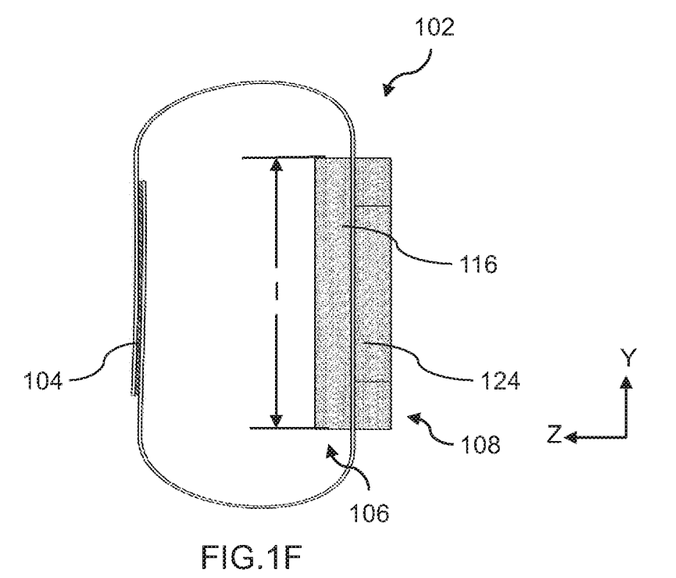
FIG. 1F illustrates a left-side view of the pressure relief apparatus of the FIG. 1A.
Figure 1G:
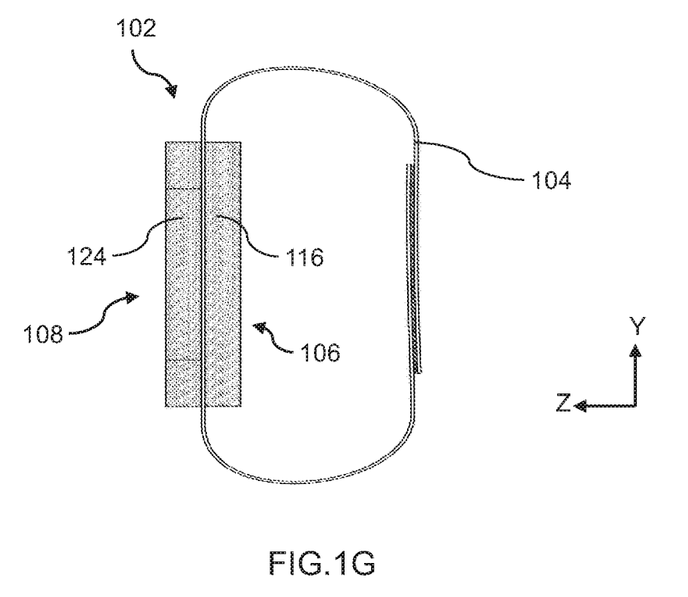
FIG. 1G illustrates a right-side view of the pressure relief apparatus of e FIG. 1A.

FIG. 1A illustrates a perspective view of a pressure relief apparatus 100 (herein after referred to as "the apparatus 100"), in accordance with an embodiment of the present disclosure. FIGS. 1B-1G illustrate front, back, top, bottom, left side and right side views of the apparatus 100, respectively. Referring to FIGS. 1A-1G, the apparatus 100 includes a body 102 and at least one fastening member 104 attached to the body 102. The apparatus 100 provides relief from pressure being applied upon a wound on a patient body. The apparatus 100 may have different sizes and shapes to be used with any size of wound at any stage. The apparatus 100 may be used for a wound or a pressure ulcer on any area of the body such as, but not limited to, shoulder blades, back, elbows, sacrum, buttocks, trochanter, heels, plantar, toes, and so forth. In some other embodiments, the apparatus 100 may also be used for wounds related to arterial insufficiency, or related to surgical wounds on substantially any part of the body where pressure is applied.

In some embodiments, the body 102 is made of a foam material such as, but not limited to polyester polyurethane foam. Further, the foam material may washable and can be easily cleaned for reuse. The foam material may also be fire retardant. In some other embodiments, the body 102 is made up of any pliable and conformable foam material that is sufficiently rugged for use in emergency medical situations. In other embodiments, the foam material may be soft on the delicate and fragile skin of a patient. Further, the foam material may allow usage of the body 102 on any acute or chronic wounds. One suitable material is a polymer foam, e.g., foamed polyurethane material, such as S82N polyester polyurethane foam. The S82N foam is characterized by a density of 32.04 +/−10% kg/m$^3$, a tensile strength of at least about 110 kPa. and an average of about 138 kPa, an elongation factor from about 90% to about 116%, a compression force deflection (25% deflection) of about 3.8 kN/M$^2$ to about 5.2 kN/M$^2$, a compression force deflection (50% deflection) of about 4.1 kN/M$^2$ to about 5.9 kN/M$^2$, a minimum 70% retention of tensile strength after 3 hours in a 105 degree-C steam autoclave, and a minimum 70% retention of tensile strength after 22 hours in a 140 degree-C steam autoclave. While a polyester polyurethane foam S82N is discussed herein, any suitable material may be used in manufacturing of the body 102. In some other embodiments, the material used in the body 102 may be a viscoelastic foam which provides the redistribution of pressure around an affected or wounded area allowing the wound to heal faster.

Referring to FIGS. 1A-1G, the body 102 includes a first part 106 that contacts or interfaces with the patient body. The body 102 also includes a second part 108 that is coupled with the first part 106. The first part 106 and the second part 108 are disposed adjacent to each other. In some embodiments, the body 102 may be comprise one piece as opposed to a first part and a second part. In some other embodiments, the first part 106 and the second part 108 are coupled to each other to form the body 102. The first part 106 and the second part 108 may be coupled by any suitable coupling methods, such as, but not limited to, adhesives, sewing, snap fasteners, Velcro, or a combination thereof. The body 102 may define a X-direction, a Y-direction, and a Z-direction in three dimensions. The X-direction is along a width "w" of the body 102, the Y-direction is along a length "l" of the body and the Z-direction is along a height "h" of the body 102.

In an embodiment, the height "h" of the body 102 of the apparatus 100 may be customized for an amount of pressure that may be expected to be applied upon the wound. For example, an apparatus for the bottom of a foot of an ambulatory patient may require a thicker body than an apparatus for the bottom of a foot of a non-ambulatory patient or an apparatus on a less pressure-bearing point, such as an elbow. In other embodiments of the present invention, the customized amount of pressure may be achieved by altering the density of the body of the apparatus. For example, in instances where a foam body is utilized, altering the density of the foam may allow for varying flexibility, support and stiffness. An apparatus for a substantially non-pressure bearing point, such as a forearm, may have a relatively thin body (e.g., to protect against incidental bumps, etc.). The body 102 may be sufficiently thick so that when the apparatus 100 compresses due to the expected amount of pressure, the wound itself should not come in contact with anything, i.e., little or no additional pressure is applied to the wound. Therefore, the apparatus 100 prevents direct contact of the wound with any surface which may be detrimental to the healing process. Furthermore, a surface area of the body 102 in contact with the patient's body may be made relatively large in comparison to the size of the wound. A relatively large surface area may redistribute pressure over a wider area, thereby reducing pressure-related problems in the surrounding healthy tissue.

In some embodiments, the body 102 may be custom shaped for the size and shape of a patient's wound, e.g., by carving a custom-sized and shaped void from a block of foam. In an embodiment, the body 102 may have a rectangular shape. In other embodiments, the body 102 may be custom shaped for larger wounds by adhesively coupling together separate subsections or layers in order to create a larger apparatus having a sufficiently large aperture, i.e., either an aperture large enough to accommodate the wound, or nearly large enough to accommodate the wound with minimal additional carving. Further, the shape of the body 102 is exemplary in nature and the body 102 may have any other shape and size according to the shape and size of the wound.

In an exemplary embodiment, the first part 106 has a substantially rectangular shape. In some other embodiments, the first part 106 may have any suitable shape, for example, but not limited to, obround, square, polygonal, oval, circular, elliptical, and so forth. The first part 106 includes a top surface 112, a bottom surface 114 opposite to the top surface 112, a pair of lateral surfaces 116 extending between the top surface 112 and the bottom surface 114, a front surface 118 extending between the pair of lateral surfaces 116, and a back surface 120 opposite to the front surface 118. The first part 106 has a length "l1" defined along the Y-direction, a width "w1" defined along the X-direction and a height "h1" defined in Z direction. In an exemplary embodiment, the bottom surface 114 contacts with the patient body. The first part 106 further defines a first aperture 110 that is sized to surround the wound. In some embodiments, the first aperture 110 is defined around a center of the first part 106. Further, the first aperture 110 may be a through aperture extending along the height "h1" of the first part 106. In alternative embodiments, the first aperture 110 may extend partially from the bottom surface 114 to a height less than the height "h1". In some embodiments, the first aperture 110 may be circular and has a radius "r1". The first aperture 110 may have a radius based on the size of the wound. In some other embodiments, the first aperture 110 may have any suitable shape such as, but not limited to, oval, elliptical and so forth. In an alternative embodiment, the first aperture 110 may have an irregular shape. The first aperture 110 may be formed during the manufacturing of the first part 106. In some other embodiments, the first aperture 110 may be carved from the first part 106.

In an exemplary embodiment, the first part 106 is made from a washable foam material. Further, the first part 106 may be made of the foam material which is soft on the delicate and fragile skin of a patient. In some other embodiments, the body 102 is made up of any pliable and conformable foam material that is sufficiently rugged to be used in emergency medical situations.

In an exemplary embodiment, the second part 108 has an obround shape. In some other embodiments, the second part 108 may have any suitable shape, for example, but not limited to, rectangular, square, polygonal, oval, circular, elliptical, and so forth. The second part 108 includes a top surface 122, a bottom surface (not shown) opposite to the top surface 122, a pair of lateral surfaces 124 extending between the top surface 122 and the bottom surface, a front surface 126 extending between the pair of lateral surfaces 124, and a back surface 128 opposite to the front surface 126. In an exemplary embodiment, the bottom surface of the second part 108 is coupled to the top surface 112 of the first part 106. The bottom surface of the second part 108 may be couple to the top surface 112 by any suitable coupling methods, such as, but not limited to, an adhesive, Velcro, sewing, snap fasteners or a combination thereof. Further, the pair of the lateral surfaces of 124 of the second part 108 may be adjacent to the pair of lateral surfaces 116 of the first part 106. The second part 108 has a width "w2" defined along the X-direction and a height "h2" defined along the Z-direction. Each of the front surface 126 and the hack surface 128 of the second part 108 has a curvilinear shape. In an embodiment, each of the front surface 126 and the back surface 128 may have a semi-circular shape. Therefore, the second part 108 has a variable length along the Y-direction. Further, the second part 108 has a minimum length "l2" and a maximum length "l3". In an exemplary embodiment, the maximum length "l3" of the second part may be substantially equal to the length "l1" of the first part 106. In some embodiments, the length "l" of the body 102, the length "l1" of the first part 106 and the maximum length "l3" of the second part 108 may be equal to each other. Further, the width "w2" of the second part 108, the width "w1" of the first part 106 and the width "w" of the body 102 may be equal to each other. A sum of the height "h2" of the second part 108 and the height "h1" of the first part 106 may be substantially equal to the height "h" of body 102. The shape and size of the second part 108 are exemplary in nature and the second part 108 may have any alternative shape and size based on the application of the apparatus 100.

In some embodiments, the second part 108 further defines a second aperture 130. The second aperture 130 may be defined around a center of the second part 108. The second aperture 130 may be a through aperture extending along the height "h2" of the second pare 108. In an alternative embodiment, the second aperture 130 may extend partially along the lateral surface 124 to a height less than the height "h2". In some embodiments, the second aperture 130 may be circular in shape and has a radius "r2". The second aperture 130 may have a radius based on the size of the wound. In some other embodiments, the second aperture 130 may have any suitable shape such as, but not limited to, oval, elliptical and so forth. In an alternative embodiment, the second aperture 130 may have an irregular shape. In another embodiment, the second aperture 130 is aligned with the first aperture 110 of the first part 106. Further, the radius "r1" of the first aperture 110 and the radius "r2" of the second aperture 130 may be substantially equal to one another. The first aperture 110 and the second aperture 130 together define an aperture 111 of the body 102. The shape and size of the aperture 111 is exemplary in nature and may vary according to shape and size of the wound. In an embodiment, the aperture 111 may be a through aperture extending along the height "h" of the body 102. In an alternative embodiment, the aperture 111 may extend partially along the Z-direction. In another embodiment, the first part 106 may only define an aperture, while the second part 108 may be devoid of any aperture. Examples wherein the aperture does not extend through the height of the body may be useful in instances where pressure relief is needed but also where a particular wound must remain covered so as to avoid infection and the like. In a further embodiment, the second part 108 may only define an aperture, while the first part 106 may be devoid of any aperture. The aperture 111 may reduce a direct pressure exerted upon the wound. The aperture 111 may also allow precise positioning of the apparatus 100 over the wound. Further, the aperture 111 may have a size which is greater than or equal to the size of wound.

In some embodiments, the bottom surface 114 of the first part 106 acts as a first surface of the body 102 and the top surface 122 of the second part 108 acts as a second surface of the body 102. In some embodiments, the body 102 is placed on the wound such that the aperture 111 surrounds the wound, and the first surface contacts with the patient body. Therefore, the body 102 relieves the pressure upon the wound and aids in the healing process. Alternatively, the top surface 122 of the second part 108 may contact the patient body. In some embodiments, each of the first part 106 and the second part 108 may be detachably secured to each other, and may be easily removed or replaced when required.

While the apparatus may include any number of fastening members, in an exemplary embodiment, the apparatus 100 includes a pair of fastening members 104 attached to the body 102. The pair of fastening members 104 detachably secures the body 102 to a portion of the patient body. In some embodiments, a portion may be carved out from the body 102 to attach the pair of fastening members 104 to the body 102. In yet another embodiment of the present invention, the body 102 further comprises a hole to accept the fastening member. In some embodiments, each of the pair of fastening members 104 is a single strap which runs continuously through the body 102. Alternatively, each of the pair of fastening members 104 may include two separate pieces. One end of each piece is attached to the body 102. Further, other ends of each piece may include any suitable attachment methods, such as, but not limited to, snap fasteners, Velcro, buttons and so forth. The pieces of each fastening member 104 may be detachably coupled to each other to secure the apparatus 100 to the patient body.

In some embodiments, the pair of fastening members 104 are integrally attached to the body 102 during manufacturing. In some other embodiments, the pair of fastening members 104 may be attached to the exterior of the body 102 after manufacture of the body 102. In exemplary embodiments, the pair of fastening members 104 are retained between the first part 106 and the second part 108 using any suitable attachment methods, for example, but not limited to, an adhesive, sewing, Velcro or a combination thereof. In yet other embodiments, the body 102 may comprise a single component as opposed to a first part 106 and a second part 108 wherein the body 102 further comprises and aperture to accept the fastening members 104. In some embodiments, each of the pair of fastening members 104 may be an adjustable strap provided with a length adjustment mechanism such as, but not limited to, a buckle, Velcro, and so forth. In some embodiments, each of the pair of fastening members 104 may be made of gauze, linen, cotton, polyester/cotton blend or any other soft fabric. In some embodiments, the fastening member may be an adhesive, wherein said adhesive adheres the apparatus to the applicable area of an individual's body to be treated. In some other embodiments, each of the pair of fastening members 104 may be of an elastic material in order to accommodate different shapes and sizes of body parts of the patient. In yet another embodiment, the material of each of the pair of fastening members 104 depends upon the mobility and the condition of the patient. Further, the size and type of the pair of fastening members 104 may depend upon space, body shape and size limitations. As illustrated in FIGS. 1A-1G, the apparatus 100 includes a pair of fastening members 104. However, the apparatus 100 may include any number of fastening members 104. In an alternative embodiment, the fastening member 104 may also be an adhesive strip disposed on any suitable location on the body 102.

In some embodiments, the apparatus 100 further includes an absorbent layer (not shown in FIGS. 1A-1G) disposed on at least a portion of the first surface of the body. The absorbent layer may be situated between the body 102 and the patient's skin, when the body 102 is secured to the patient. The absorbent layer may absorb exudate from the wound and prevent infection. Therefore, the absorbent layer may aid in the healing process. In some embodiments, the absorbent layer is attached to the first surface via an adhesive. In some other embodiments, the absorbent layer may be detachably attached to the apparatus 100 by use of a fastener, such as, but not limited to, Velcro, snap fasteners and so forth. The absorbent layer may be easily removed or replaced when required. For example, when the absorbent layer becomes contaminated, the apparatus 100 may be temporarily removed from the wound. The absorbent layer can be replaced with a clean absorbent layer. The apparatus 100 with the clean absorbent layer can be then applied around the wound again. The absorbent layer may be made of cotton fiber or any other similar fiber which can absorb the exudate from the wound.

In alternative embodiments, the apparatus 100 may be provided in one of a variety of shapes, colors and sizes, customized to the patient. For example, size and shape may be chosen based upon the patient's specific wound and wound location, and color may be chosen based on factors, such as, aesthetics (e.g., to match a patient's skin tone) or clinical needs (e.g., to make the presence of exudate more noticeable). In some embodiments, the body 102 is made up of a transparent or translucent material to allow continuous monitoring on the condition of the wound. The transparent or translucent material may also allow precise positioning of the body 102 with respect to the wound.

A manner of securing the apparatus 100 to the patient may depend upon the location of the wound. For example, treating a wound located on a patient's back may involve securing the apparatus 1.00 with the fastening members 104 or an adhesive backing on the abdomen, and optionally further securing the apparatus to the patient's undergarment. In another example, treating a wound on a trochanter (e.g., a hip location) may involve securing the apparatus 100 with an adhesive backing, and optionally further securing the apparatus 100 to the patient's undergarment. In another example, treating a wound on a heel may involve securing the apparatus 100 with the pair of fastening members 104 on the top, center and bottom, around the patient's ankle and heel. In another example, treating a wound on a toe may involve securing the apparatus 100 with an adjustable strap.

In some embodiments, the apparatus 100 is used in wound care by a nurse or caregiver, under doctor's orders. Ordinarily, a dressing is applied first, and then the apparatus 100 is customized for the size and shape of the patient's wound as dressed, taking care to substantially reduce or eliminate a possibility that the apparatus 100 would apply unwanted pressure to the wound. For example, the apparatus 100 can be customized to provide a minimum clearance between the apparatus 100 and the dressing. Then the apparatus 100 is placed over the wound and secured to the patient, e.g., by usage of an adjustable belt, or a hook and loop fastener (e.g., a Velcro brand fastener). The apparatus 100 may offload pressure from a wound and thereby help the wound heal or help prevent the wound from getting worse.

The apparatus 100 is reusable and therefore soiled portions (e.g., portions that have contacted exudate) may be cleansed and/or sterilized between uses; or soiled portions may be removed, discarded, and replaced with a clean portion. In some embodiments, at least a portion of the apparatus 100 may be made impermeable to fluids, e.g., by use of a coating, or a cover, or by braising or cauterizing at least a portion of the foam surface. Reuse after cleaning and/or sterilization is more suitable for relatively lightly-soiled portions. Relatively heavily-soiled portions are more suitable to be discarded. In some embodiments, the apparatus 100 may be sterilized completely before it is first affixed to a patient.

Figure 2:
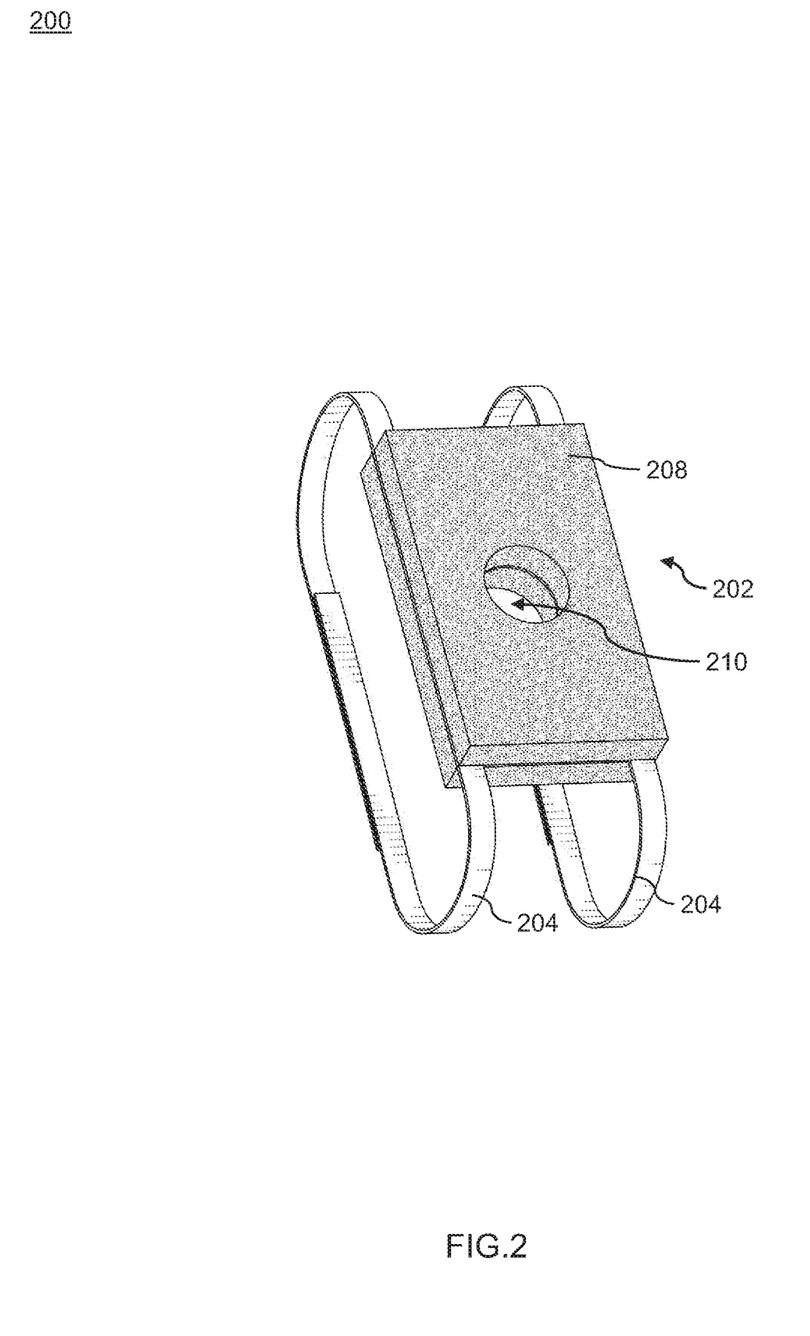
FIG. 2 illustrates an oblique view of a pressure relief apparatus, in accordance with an embodiment of the present disclosure.

FIG. 2 illustrates an oblique view of a pressure relief apparatus 200 (hereinafter referred to as "the apparatus 200"), in accordance with an embodiment of present invention. The apparatus 200 includes a body 202 and a pair of straps 204 as fastening members. The body 202 is made of a washable foam material. In some embodiments, the foam material is fire retardant. In some other embodiments, the body 102 is made up of any pliable and conformable foam material that is sufficiently rugged for use in emergency medical situations. One suitable material is a polymer foam, e.g., a foamed polyurethane material, such as S82N polyester polyurethane foam. The body 202 has a substantially rectangular shape. The body 202 includes a first surface (not shown) and a second surface 208 opposite to the first surface. The first surface contacts with the patient body. The first surface may be soft on delicate and fragile skin. The body 202 further defines an aperture 210 that is sized to surround the wound. In some embodiments, the aperture 210 may be a through aperture extending along a height of the body 202. In some other embodiments, the aperture 210 may extend partially along the height of the body 202. Further, the aperture 210 may have a circular shape. The aperture 210 may have a diameter which is equal to or greater than the size of the wound. In an exemplary embodiment, the pair of straps 204 secure the body 202 to the patient body. In some embodiments, each of the pair of straps 204 is a single strip which runs continuously through the body 202. Alternatively, each of the pair of straps 204 may be two separate pieces with each piece attached to the body 202. Alternatively, the pair of straps 204 may be of any form that can retain the apparatus 200 on the patient body. In some embodiments, each of the pair of straps 204 is made of a soft fabric, such as cotton, linen, and so forth. In another embodiment, the material of each of the pair of straps 204 may depend upon the mobility and the condition of the patient. Further, the size and type of the pair of straps 204 may depend upon space, body shape and size limitations.

In some embodiments, the apparatus 200 includes an absorbent layer disposed on at least a portion of the first surface. The absorbent layer absorbs exudate from the wound. In some embodiments, the absorbent layer is detachably attached to the first surface via an adhesive or any other coupling mechanism. In alternative embodiments, the absorbent layer may completely cover the first surface.

In some embodiments, the apparatus 200 may be custom shaped for the size and shape of a patient's wound, e.g., by carving a custom-sized and shaped void from a block of foam. In other embodiments, the apparatus 200 may be custom shaped for larger wounds by adhesively coupling together separate subsections or layers in order to create a larger apparatus having a sufficiently large aperture, i.e., either an aperture large enough to accommodate the wound, or nearly large enough to accommodate the wound with minimal additional carving.

Further, a height of the apparatus 200 may be customized for an expected amount of pressure that may be expected to be applied upon the wound. For example, an apparatus for the bottom of a foot of an ambulatory patient may be thicker than an apparatus for the bottom of a foot of a non-ambulatory patient or of an apparatus on a less pressure-bearing point such as an elbow. An apparatus for a substantially non-pressure bearing point, such as a forearm, may have a relatively thin apparatus (e.g., to protect against incidental bumps, etc.). The apparatus 200 may be sufficiently thick so that when the apparatus 200 compresses due to the expected amount of pressure, the wound itself should not come in contact with anything, i.e., little or no additional pressure is applied to the wound.

Furthermore, a surface area of the apparatus 200 in contact with the patient's body may be made relatively large in comparison to the size of the wound. A relatively large surface area may redistribute pressure over a wider area, thereby reducing pressure-related problems in the surrounding healthy tissue.

Figure 3:
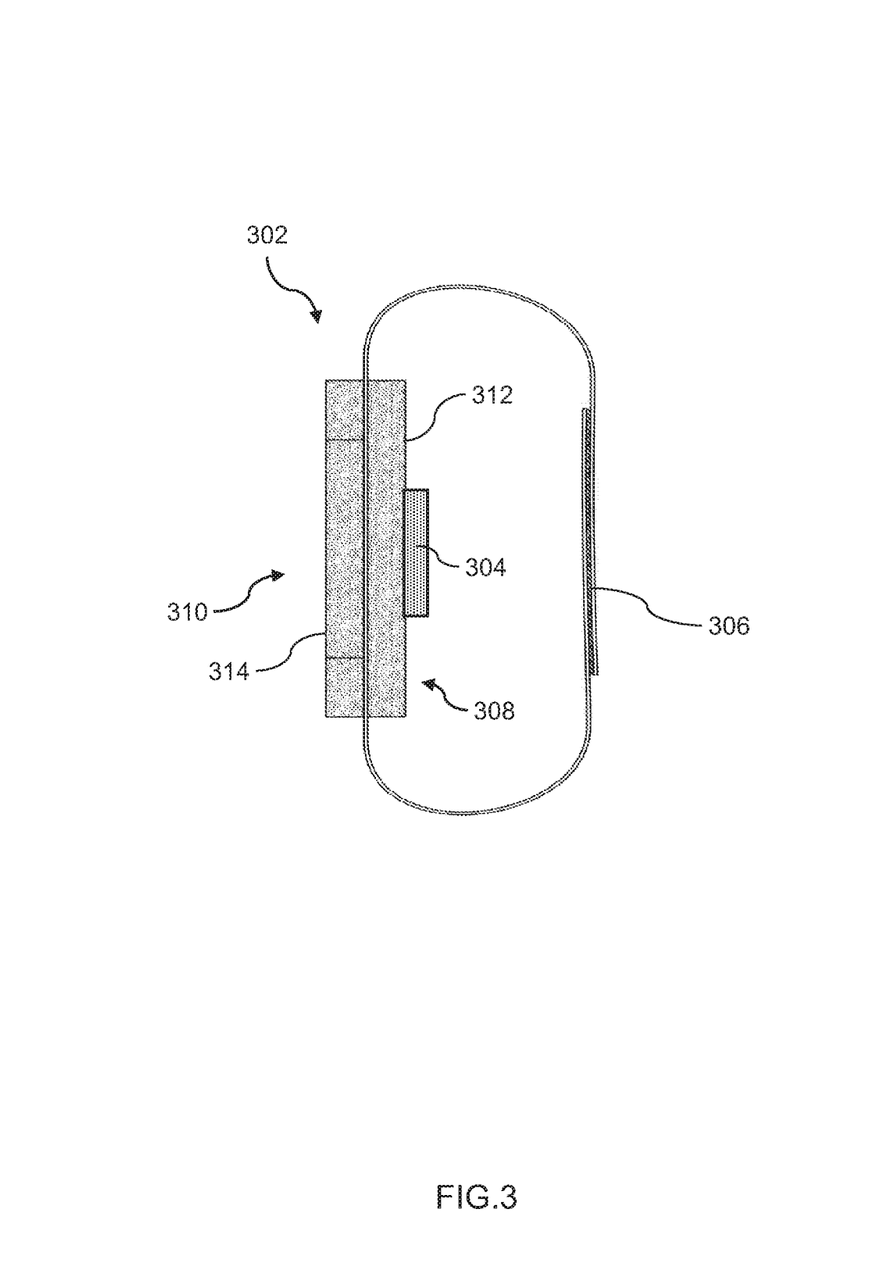
FIG. 3 illustrates a right-side view of a pressure relief apparatus, in accordance with an embodiment of the present disclosure.

FIG. 3 illustrates a right-side view of a pressure relief apparatus 300 (herein after referred to as "the apparatus 300") according an embodiment of the present invention. The apparatus 300 includes a body 302, an absorbent layer 304 and at least one fastening member 306. The body 302 is made of a washable foam material. In some embodiments, the foam material is fire retardant. In some other embodiments, the body 302 is made up of any pliable and conformable foam material that is sufficiently rugged to use in emergency medical situations. One suitable material is a polymer foam, e.g., a foamed polyurethane material. The body 302 includes a first part 308 and a second part 310. The first part 308 contacts with the patient body. In an exemplary embodiment, the first part 308 has a rectangular shape. The first part 308 defines an aperture (not shown in FIG. 3) that is sized to surround the wound. In some embodiments, the aperture is defined centrally within the first part 308. In an exemplary embodiment, the aperture has a circular shape. In some embodiments, the aperture may extend through the first part 308 and the second part 310. In some other embodiments, the aperture may extend partially through the body 302. In an exemplary embodiment, the first part 308 is made from the washable foam material. The first part 308 is made of a foam material which is soft on delicate and fragile skin, and therefore comfortable to be used on the wounds. The first part 308 and the second part 310 may be coupled to each other via any suitable coupling methods, such as, but not limited to, adhesive, sewing. Velcro, and so forth. In an exemplary embodiment, the second part 310 has an obround shape. In some embodiments, a length of the second part is equal to a length of the first part. Further, a width of each of the first part 308 and the second part 310 is equal. In some embodiments, lateral surfaces of the second part 310 may abut lateral surfaces of the first part 308.

The body 302 further includes a first surface 312 defined by the first part 308 and a second surface 314 opposite to the first surface 312. The second surface 314 is defined by the second part 310. The first surface 312 contacts with the patient body. In some embodiments, the fastening member 306 is retained between the first part 308 and the second part 310. The body 302 may include a passage for the fastening member 306 between the first part 308 and second part 310. In some other embodiments, the fastening member 306 may have open ends that extend partially between the first part 308 and the second part 310.

The body 302 further defines an aperture (not shown in FIG. 3) extending along a height of the body 302. In some embodiments, the aperture may extend partially along the height of the body 302. In an exemplary embodiment, the aperture surrounds the wound. Further, size and shape of the aperture may depend upon on the wound. In some embodiments, the aperture may be located centrally in the body 302 extending from the first surface 312.

The apparatus 300 includes the absorbent layer 304 disposed on at least a portion of the first surface 312. The absorbent layer 304 absorbs exudate from the wound. The absorbent layer 304 may be washable, re-useable, removable, disposable, and replaceable. The absorbent layer 304 may include cotton or any other cotton-like absorbent material. The absorbent layer 304 may be detachably attached to the apparatus 300 by use of an adhesive, or a fastening mechanism, such as Velcro, snap fasteners. In some embodiments, when the absorbent layer 304 becomes contaminated, the apparatus 300 may be temporarily removed from the wound, thereby allowing the removal of the absorbent layer 304 and an attachment of a clean absorbent layer 304. The apparatus with clean absorbent layer can be put over or around the wound again. Further, the absorbent layer 304 may be disposed around the aperture.

Figure 4:
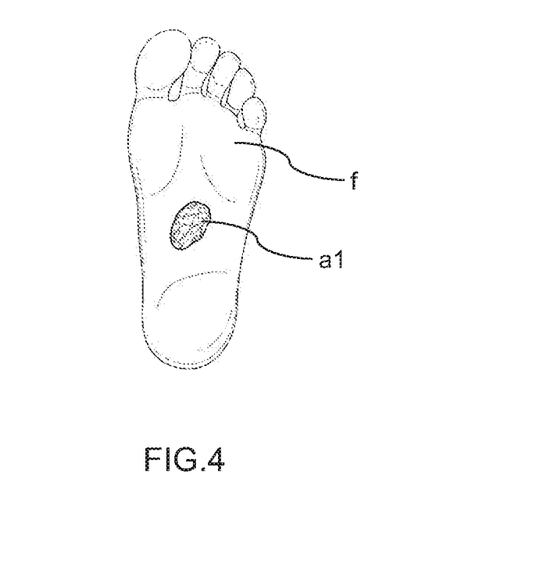
FIG. 4 illustrates a wound in a foot.
Figure 5:
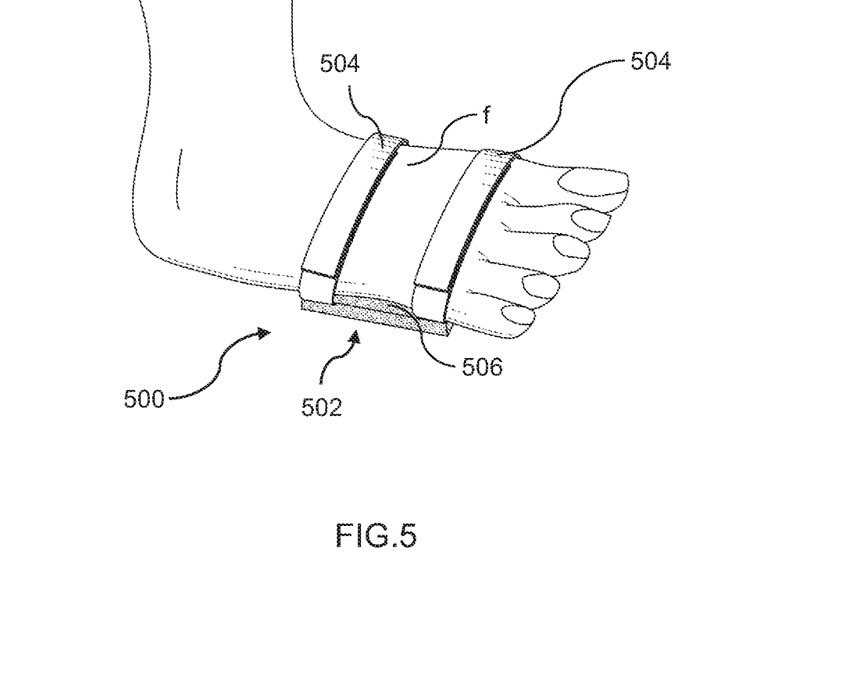
FIG. 5 illustrates a pressure relief apparatus secured to the foot of FIG. 4.

FIG. 4 illustrates a wound "a1" at the bottom surface of a foot "f" of a patient. FIG. 5 illustrates a pressure relief apparatus 500 (hereinafter referred to as "the apparatus 500") surrounding the wound "a1". The apparatus 500 is similar to the apparatus 100, illustrated in FIGS. 1A-1G. Therefore, to facilitate understanding, parts illustrated in FIGS. 1A to 1G, are provided with the corresponding referral numerals in FIG. 5. Alternatively, the apparatus 500 may be similar to the apparatus 200 (shown in FIG. 2) or the apparatus 300 (shown in FIG. 3). Though the wound "a1" is illustrated as being located at the bottom of the foot "f", the wound "a1" may be located on any body part such as, a patient's back, a trochanter (e.g., a hip location), a heel, a toe, and so forth. The wound "a1" may include a cut, a sore, a burn, etc. In some other embodiments, the wound "a1" may be a pressure ulcer on any area of the body, such as shoulder blades, back, elbows, sacrum, buttocks, trochanter, heels, plantar, toes, and so forth. In further embodiments, the wound "a1" may be related to arterial insufficiency, or related to surgical wounds on substantially any part of the body where pressure is applied. In alternative embodiments, the wound "a1" may be any type of diabetic wound. Further, the wound "a1" may have different shapes and sizes. In some embodiments, the wound "a1" may ooze an exudate before it is completely healed. The wound "a1" may be cleaned and covered with a dressing before the apparatus 500 is used on the wound. As shown in FIG. 5, the apparatus 500 covers the wound "a1". The apparatus 500 is positioned such that the wound "a1" is surrounded by an aperture (not shown in FIG. 5) defined by a body 502 of the apparatus 500. The fastening members 504 may retain the apparatus 500 around the wound "a1". A first part 506 of the apparatus 500 contacts with the foot "f". The body 502 may distribute the pressure along a part of the patient body, such as the foot "f", and reduce or eliminate a pressure exerted upon the wound "a1". Therefore, the apparatus 500 may aid in the healing process and reduce chances of infection. Further, a thickness of the body 502 may depend upon the type of the wound "a1" and mobility of the patient. In some embodiments, if the patient is mobile, a thicker body may be required as compared to a patient who is bedridden. In an embodiment, the apparatus 500 may support the foot "f" on any surface, such as a bed, a floor, and so forth. The apparatus 500 may prevent direct contact of the wound "a1" with any surface which may delay the healing process, or cause additional damage to the wound "a1".

Figure 6:
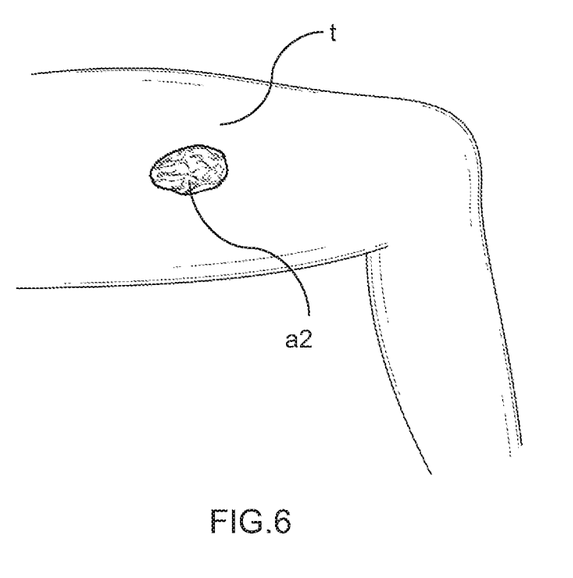
FIG. 6 illustrates a view of a wound on a thigh.
Figure 7:
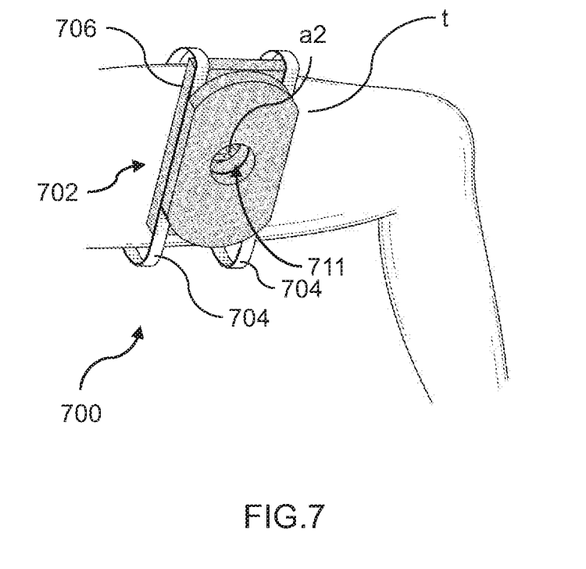
FIG. 7 illustrates a pressure relief apparatus secured to the thigh of FIG. 6.

FIG. 6 illustrates a wound "a2" on a thigh "t" of a patient. FIG. 7 illustrates a pressure relief apparatus 700 (hereinafter referred to as "the apparatus 700") surrounding the wound "a2". The apparatus 700 is similar to the apparatus 100, illustrated in FIGS. 1A-1G. Therefore, to facilitate understanding, parts illustrated in FIGS. 1A to 1G are provided with the corresponding referral numerals in FIG. 7. Alternatively, the apparatus 700 may be similar to the apparatus 200 (shown in FIG. 2) or the apparatus 300 (shown in FIG. 3). Though the wound "a2" is illustrated as being located on the thigh "t" of a patient, the wound "a2" may be located on any body part such as, a patient's back, a trochanter (e.g., a hip location), a heel, a toe and so forth. The wound "a2" may include a cut, a sore, a burn, etc. In some other embodiments, the wound "a2" may be a pressure ulcer on arty area of the body such as, shoulder blades, back, elbows, sacrum, buttocks, trochanter, heels, plantar, toes, and so forth. In further embodiments, the wound "a2" may be related to arterial insufficiency, or related to surgical wounds on substantially any part of the body where pressure is applied. In alternative embodiments, the wound "a2" may be a diabetic wound. In some embodiments, the wound "a2" may ooze an exudate before it is completely healed. The wound "a2" may be cleaned and covered with a dressing before the apparatus 700 is used on the wound "a2". As shown in FIG. 7, the apparatus 700 surrounds the wound "a2". Specifically, the apparatus 700 is positioned, such that the wound "a2" is surrounded by an aperture 711 defined by a body 702 of the apparatus 700. The aperture 711 may allow precise positioning of the apparatus 700 upon the wound. Further, the aperture 711 reduces the pressure being exerted upon the wound. As shown in FIG. 7, the apparatus 700 is positioned on the thigh "t", such that the wound "w2" is uncovered. The fastening member 704 may secure the apparatus 700 to the thigh "t", while retaining the apparatus 700 around the wound "a2". A first part 706 of the apparatus 700 contacts with the thigh "t". The body 702 may distribute pressure along a part of the patient body, and reduce or eliminate a pressure exerted upon the wound "a2". Therefore, the apparatus 700 may prevent any unexpected pressure on the wound "a2" any sudden moment of the thigh "t". In some other embodiments, the apparatus 700 may assist the patient in sleeping by reducing or eliminating any pressure applied on the wound "a2". Therefore, the apparatus 700 may aid in the healing process and reduces chances of infection. Further, a thickness of the body 702 may depends upon the type of the wound "a2" and mobility of the patient.

While the foregoing is directed to embodiments of the present disclosure, other and further embodiments of the present disclosure may be devised without departing from the basic scope thereof. It is understood that various embodiments described herein may be utilized in combination with any other embodiment described, without departing from the scope contained herein. Further, the foregoing description is not intended to be exhaustive or to limit the disclosure to the precise form disclosed. Modifications and variations are possible in light of the above teachings or may be acquired from practice of the disclosure. Certain exemplary embodiments may be identified by use of an open-ended list that includes wording to indicate that the list items are representative of the embodiments and that the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the disclosure unless explicitly described as such. Also, as used herein, the article "a" is intended to include one or more items. Where only one item is intended, the term "one" or similar language is used. Further, the terms "any of" followed by a listing of a plurality of items and a plurality of categories of items, as used herein, are intended to include "any of," "any combination of," "any multiple of," and/or "any combination of multiples of" the items and/or the categories of items, individually or in conjunction with other items and/or other categories of items.

Moreover, the claims should not be read as limited to the described order or elements unless stated to that effect. In addition, use of the term "means" in any claim is intended to invoke 35 U.S.C. § 112(f), and any claim without the word "means" is not so intended.

What is claimed is:

1. A pressure relief apparatus configured for use in relieving pressure on a wound on a patient, the pressure relief apparatus comprising:
    a first part having a first surface, a second surface opposite the first surface, and a first through aperture that is centrally disposed and extends through the first part between the first surface and second surface, wherein the first surface is rectangular having two long edges that are each parallel to a long axis of the first part and two short edges that are each parallel to a short axis of the first part;
    a second part having a third surface, a fourth surface opposite the third surface, and a second through aperture that is centrally disposed and extends through the second part between the third surface and the fourth surface, wherein the second surface of the first part is coupled to the third surface of the second part wherein the first through aperture and second through aperture are arranged to form a single centrally disposed through aperture that extends from the first surface of the first part to the fourth surface of the second part;
    a first fastener continuously disposed along an entirety of a first long edge of the first part between the second surface of the first part and the third surface of the second part, the first fastener having a long axis that is parallel to the long axis of the first part, wherein the first fastener is configured to detachably secure the pressure relief apparatus around the wound; and
    a second fastener continuously disposed along an entirety of a second long edge of the first part between the second surface of the first part and the third surface of the second part, the second fastener having a long axis that is parallel to the long axis of the first part, wherein the second fastener is configured to detachably secure the pressure relief apparatus around the wound, and
    wherein either the first surface or the fourth surface is configured to alternatively contact the patient during use of the pressure relief apparatus
    wherein the first and second parts form a pliable body configured to be detachably securable to the patient by the first and second fasteners.

2. The pressure relief apparatus of claim 1, further comprising an absorbent layer disposed along at least a portion of the first surface, wherein the absorbent layer is configured to absorb exudate from the wound.

3. The pressure relief apparatus of claim 1, wherein the pliable body comprises a fire retardant material.

4. The pressure relief apparatus of claim 1, wherein the pliable body comprises a polyester polyurethane foam.

5. The pressure relief apparatus of claim 1, wherein the pliable body has a rectangular shape.

6. The pressure relief apparatus of claim 2, wherein the absorbent layer is removably coupled to the pliable body.

7. The pressure relief apparatus of claim 2, wherein the absorbent layer is made of an absorbent fiber.

8. The pressure relief apparatus of claim 1, wherein the third surface of the second part is coupled with the second surface of the first part using one or more of adhesive, sewing, fastener, or combination thereof.

9. The pressure relief apparatus of claim 8, wherein the second through aperture is aligned with the first through aperture.

10. The pressure relief apparatus of claim 8, further comprising an absorbent layer disposed along at least a portion of the first surface of the first part around the first through aperture, wherein the absorbent layer is configured to absorb exudate from the wound.

11. The pressure relief apparatus of claim 10, wherein the absorbent layer is removably coupled to the first surface.

12. The pressure relief apparatus of claim 8, wherein the second surface is rectangular.

13. The pressure relief apparatus of claim 8, wherein the third surface is obround.

14. The pressure relief apparatus of claim 1, wherein each of the first and second fasteners comprises an adjustable strap.

15. The pressure relief apparatus of claim 1, wherein the pliable body comprises a washable foam material.

16. The pressure relief apparatus of claim 15, wherein each of the first and second fasteners is retained between the first part and the second part.

17. The pressure relief apparatus of claim 1, wherein the fourth surface has an obround shape.

* * * * *